United States Patent [19]

Leong

[11] Patent Number: 5,256,765
[45] Date of Patent: Oct. 26, 1993

[54] BIODEGRADABLE POLY(PHOSPHATE ESTERS)

[75] Inventor: Kam W. Leong, Perry Hall, Md.

[73] Assignee: The Johns Hopkins University School of Medicine, Baltimore, Md.

[21] Appl. No.: 856,469

[22] Filed: Mar. 24, 1992

Related U.S. Application Data

[62] Division of Ser. No. 321,360, Mar. 9, 1989, Pat. No. 5,194,581.

[51] Int. Cl.⁵ .............................................. C08G 79/02
[52] U.S. Cl. ................................... 528/398; 528/10; 528/30; 528/167; 528/271; 528/391; 528/400

[58] Field of Search ................... 528/10, 30, 167, 271, 528/391, 398, 400

[56] References Cited

U.S. PATENT DOCUMENTS

3,285,863 11/1966 McConnell et al. ............... 528/167
3,927,231 12/1975 Desitter et al. ..................... 427/390

Primary Examiner—John Kight, III
Assistant Examiner—T. Mosley
Attorney, Agent, or Firm—Spensley Horn Jubas & Lubitz

[57] ABSTRACT

A pharmaceutical composition comprising a therapeutic agent, together with a polymeric delivery vehicle, the vehicle being made of poly(phosphoesters).

7 Claims, 4 Drawing Sheets

BIODEGRADABLE POLY(PHOSPHATE ESTERS)

This is a division of application Ser. No. 07/321,360, filed on Mar. 9, 1989, U.S. Pat. No. 5,194,581.

BACKGROUND OF THE INVENTION

1. Field of the Invention

The present invention relates to poly(phosphoesters) and methods of using these polymers.

2. Description of the Background Art

Many polymeric materials have been used as components of devices for diagnosis or therapy, and they have made a significant impact on the clinical success of implant technology. These materials have been used as, for example, orthopedic devices, ventricular shunts, drug-carriers, contact lens', heart valves, sutures, and burn dressings. These polymers can be non-biodegradable or biodegradable.

In traditional drug delivery, it has long been recognized that tablets, capsules, and injections may not be the best mode of administration. These conventional routes often involve frequent and repeated doses, resulting in a "peak and valley" pattern of therapeutic agent concentration. Since each therapeutic agent has a therapeutic range above which it is toxic and below which it is ineffective, a fluctuating therapeutic agent concentration may cause alternating periods of ineffectiveness and toxicity. For this reason, controlled release provides a way of maintaining the therapeutic agent level within the desired therapeutic range for the duration of treatment. Using a polymeric carrier is one effective means to deliver the therapeutic agent locally and in a controlled fashion (Langer, et al., *Rev. Macro. Chem. Phys.*, C23(1), 61, 1983). As a result of less total drug required, systemic side effects can be minimized.

Polymers have been used as carriers of the therapeutic agents to effect a localized and sustained release (*Controlled Drug Delivery*, Vol. I and II, Bruck, S. D., (ed.), CRC Press, Boca Raton, Fla., 1983; *Novel Drug Delivery Systems*, Chien, Y. W., Marcel Dekker, New York, 1982). These therapeutic agent delivery systems simulate infusion and offer the potential of enhanced therapeutic efficacy and reduced systemic toxicity.

For a non-biodegradable matrix, the steps leading to release of the therapeutic agent are water diffusion into the matrix, dissolution of the therapeutic agent, and out-diffusion of the therapeutic agent through the channels of the matrix. As a consequence, the mean residence time of the therapeutic agent existing in the soluble state is longer for a non-biodegradable matrix than for a biodegradable matrix where a long passage through the channels is no longer required. Since many pharmaceuticals have short half-lives it is likely that the therapeutic agent is decomposed or inactivated inside the non-biodegradable matrix before it can be released. This issue is particularly significant for many bio-macromolecules and smaller polypeptides, since these molecules are generally unstable in buffer and have low permeability through polymers. In fact, in a non-biodegradable matrix, many bio-macromolecules will aggregate and precipitate, clogging the channels necessary for diffusion out of the carrier matrix. This problem is largely alleviated by using a biodegradable matrix which allows controlled release of the therapeutic agent.

Biodegradable polymers differ from non-biodegradable polymers in that they are consumed or biodegraded during therapy. This usually involves breakdown of the polymer to its monomeric subunits, which should be biocompatible with the surrounding tissue. The life of a biodegradable polymer in vivo depends on its molecular weight and degree of cross-linking; the greater the molecular weight and degree of crosslinking, the longer the life. The most highly investigated biodegradable polymers are polylactic acid (PLA), polyglycolic acid (PGA), copolymers of PLA and PGA, polyamides, and copolymers of polyamides and polyesters. PLA, sometimes referred to as polylactide, undergoes hydrolytic de-esterification to lactic acid, a normal product of muscle metabolism. PGA is chemically related to PLA and is commonly used for absorbable surgical sutures, as is PLA/PGA copolymer. However, the use of PGA in sustained-release implants has been limited due to its low solubility in common solvents and subsequent difficulty in fabrication of devices.

An advantage of a biodegradable material is the elimination of the need for surgical removal after it has fulfilled its mission. The appeal of such a material is more than simply for convenience. From a technical standpoint, a material which biodegrades gradually and is excreted over time can offer many unique advantages.

A biodegradable therapeutic agent delivery system has several additional advantages: 1) the therapeutic agent release rate is amenable to control through variation of the matrix composition; 2) implantation can be done at sites difficult or impossible for retrieval; 3) delivery of unstable therapeutic agents is more practical. This last point is of particular importance in light of the advances in molecular biology and genetic engineering which have lead to the commercial availability of many potent bio-macromolecules. The short in vivo half-lives and low GI tract absorption of these polypeptides render them totally unsuitable for conventional oral or intravenous administration. Also, because these substances are often unstable in buffer, such polypeptides cannot be effectively delivered by pumping devices.

In its simplest form, a biodegradable therapeutic agent delivery system consist of a dispersion of the drug solutes in a polymer matrix. The therapeutic agent is released as the polymeric matrix decomposes, or biodegrades into soluble products which are excreted from the body. Several classes of synthetic polymers, including polyesters (Pitt, et al., in *Controlled Release of Bioactive Materials*, R. Baker, Ed., Academic Press, New York, 1980); polyamides (Sidman, et al., *Journal of Membrane Science*, 7:227, 1979); polyurethanes (Maser, et al., *Journal of Polymer Science, Polymer Symposium*, 66:259, 1979); polyorthoesters (Heller, et al., *Polymer Engineering Science*, 21:727, 1981); and polyanhydrides (Leong, et al., *Biomaterials*, 7:364, 1986) have been studied for this purpose.

By far most research has been done on the polyesters of PLA and PLA/PGA. Undoubtedly, this is a consequence of convenience and safety considerations. These polymers are readily available, as they have been used as biodegradable sutures, and they decompose into non-toxic lactic and glycolic acids. However, a major problem with these polymers is that it is often difficult to control and predict their degradation.

Polyorthoesters and polyanhydrides have been specifically designed for controlled release purposes. While these polymers are promising, they also have significant drawbacks. For example, polyorthoesters biodegrade in a desirable manner only if additives are included in the matrix. By taking advantage of the pH dependence of the rate of orthoester cleavage, preferential hydrolysis at the surface is achieved by either the addition of basic substances to suppress degradation in bulk, or the incorporation of acidic catalysts to promote surface degradation. Unfortunately, these additives often lead to unnecessary complications in terms of release behavior and biocompatibility.

The polyanhydrides, on the other hand, are unstable even in the solid state. In addition, the poor solubility of the hydrophobic polyanhydrides also render characterization and fabrication difficult. Hence there exists the need for new biodegradable polymers.

The biodegradable matrix of the invention also finds broad utility as a transient prosthetic support in orthopedic applications. For centuries, physicians have attempted to repair and replace various components of the skeletal system. These attempts have utilized various kinds of materials including bone, ivory, collagen, wood, metals, alloys, ceramics, glasses, corals, carbons, polymers, and composites of materials as bone prostheses.

Ideally, the bone prosthesis should be a material that is biologically inert, readily available, easily adaptable to the site in terms of shape and size, and replaceable by the host bone. Replacement of the prothesis by the host bone necessitates that the substitute be biodegradable.

The different elastic moduli of the prior art prosthetic implants versus that of bone often causes cortical bone to atrophy. The theoretical advantage of gradual load transfer from the bone plate to the bone and the elimination of the need for surgical removal after the healing of a fracture would make an absorbable osteosynthesis material extremely useful. As a temporary support in a load-bearing area of an articular joint, a resorbable porous material also has the advantage of preventing further destruction of cartilage defects and promoting bone and cartilage-forming cells. Hence, a need exists for a biodegradable prosthesis of sufficient post-implantation strength and rigidity to provide structural support.

SUMMARY OF THE INVENTION

The present invention pertains to a biodegradable composition useful as a structural prosthesis and a therapeutic agent delivery vehicle and methods for its manufacture and use. The composition comprises a biocompatible poly(phosphoester) matrix, prepared in preselected dimensions and configurations, which predictably degrades in vivo into non-toxic residues. The method of using the composition as an implant and prosthesis comprises the step of introducing a specifically configured composition into an individual in vivo at a predetermined site.

Although it is preferred that the polymers of the invention be biodegradable and in matrix form, these characteristics are not essential for the polymers.

The composition of the invention, through its transient in vivo presence, provides a matrix which persists for a period of time sufficient to achieve a medical effect, essentially lacks host toxicity upon degradation, provides mechanical strength, and is readily fabricated.

DETAILED DESCRIPTION

The present invention is directed to compositions useful as prostheses and as therapeutic agent delivery vehicles. These compositions comprise a biodegradable, biocompatible class of poly(phosphoesters). The polymers are biodegradable because of the hydrolyzable phosphoester, or P(O)—O—C bond, in the backbone. With the phosphoester linkage, the polymers can be classified as polyphosphates, polyphosphonates, or polyamidophosphates, depending on the structure of the pendant groups. With the phosphorous atom existing in the trivalent state, the polymers can be either polyphosphites or polyphosphonites.

Preferred are compositions comprising a biodegradable poly-phosphate or polyphosphonate matrix which have the general formula:

wherein R and R', are preferably organic or organometallic moieties and n is from about 10 to about $10^5$.

The R' group can be a therapeutic agent or, alternatively, can be selected from the group consisting of:

wherein $R_1$ is alkyl, halogen, nitro, hydroxyl, amino, carboxyl, alkoxy, or combinations thereof, $R_2$ is oxygen or N—$CH_3$, and a ranges from 2 to 6, b ranges from 10 to 100, d ranges from 2 to 16, f ranges from 1 to 6, and m ranges from 1 to 2.

Other R groups that function equivalently to these R groups are within the scope of the invention.

The R group can be a therapeutic agent or, alternatively, can be selected from the group consisting of:

$$-NH-R_1, -S-R_1, -O-\overset{O}{\underset{\|}{C}}-R_1$$

$$-OC_pH_{2p+1} \quad -C_pH_{2p+1} \quad -O-CH_2-\underset{\underset{CO_2H}{|}}{CH}-NH_2$$

$$-H, -Cl, -O-R_3$$

wherein $R_1$ is alkyl, halogen, nitro, hydroxyl, amino, carboxyl, alkoxy, or combinations thereof, $R_3$ is and p ranges from 1 to 16.

Other R groups that function equivalently to these R groups are within the scope of the invention.

It is also possible for R and R' to be the same or different therapeutic agent.

Other R groups that function equivalently to these R groups are within the scope of the invention.

The common synthesis and chemical structures of polyphosphates and polyphosphonates are shown in Eqs. 1 and 2, respectively. On hydrolysis the polymers decompose into monomeric phosphates and diols (Eq. 3). However, because of the hydrolytic instability of the phosphorous ester bond, there have not been any commercial applications for these polymers (Sandler, et al., in *Polymer Synthesis*, Vol. 1, Chap. 13, Academic Press, New York, 1974). It is this instability, however, which the present inventor discovered, renders these polymers attractive for achieving a medical effect for both transient structural prosthesis and therapeutic agent controlled release applications.

(Eq. 1)

(Eq. 2)

(Eq. 3)

$$H_3PO_4 + ROH + HO-R'-OH$$

In comparing the hydrolytic reactivity of different carbonyl bonds, the phosphorous ester is comparable to, or slightly more reactive than, the carboxylic ester. Thus, this water labile linkage provides the basis for a versatile delivery system.

A wide range of degradation rates can be obtained by adjusting the hydrophobicities of the backbones of the polymers and yet the biodegradability is assured. This can be achieved by varying the functional groups R or R'. The combination of a hydrophobic backbone and a hydrophilic linkage also leads to heterogeneous degradation as cleavage is encouraged, but water penetration is resisted.

The polyphosphates and polyphosphonates of the invention show favorable mechanical strength because of the high molecular weights obtainable. Average molecular weight of up to 600,000 has been obtained by an interfacial polymerization (Sandler, et al., ibid). This high molecular weight leads to transparency, and film and fiber properties. It has also been observed that the P—O—C group provides a plasticizing effect, which lowers the glass transition temperature of the polymer and confers solubility in organic solvents. Both effects are desirable for fabrication of the composition.

The term "therapeutic agent" as used herein for the compositions of the invention includes, without limitation, drugs, radioisotopes, immunomodulators, and lectins. Similar substances are within the skill of the art. The term "individual" includes human as well as non-human animals.

The drugs with which can be incorporated in the compositions of the invention include non-proteinaceous as well as proteinaceous drugs. The term "non-proteinaceous drugs" encompasses compounds which are classically referred to as drugs such as, for example, mitomycin C, daunorubicin, vinblastine, AZT, and hormones. Similar substances are within the skill of the art.

The proteinaceous drugs which can be incorporated in the compositions of the invention include immunomodulators and other biological response modifiers. The term "biological response modifiers" is meant to encompass substances which are involved in modifying the immune response in such manner as to enhance the particular desired therapeutic effect, for example, the destruction of the tumor cells. Examples of immune response modifiers include such compounds as lymphokines. Examples of lymphokines include tumor necrosis factor, the interleukins, lymphotoxin, macrophage activating factor, migration inhibition factor, colony stimulating factor and the interferons. Interferons which can be incorporated into the compositions of the invention include alpha-interferon, beta-interferon, and gamma-interferon and their subtypes. In addition, peptide or polysaccharide fragments derived from these proteinaceous drugs, or independently, can also be incorporated. Also, encompassed by the term "biological response modifiers" are substances generally referred to as vaccines wherein a foreign substance, usually a pathogenic organism or some fraction thereof, is used to modify the host immune response with respect to the pathogen to which the vaccine relates. Those of skill in the art will know, or can readily ascertain, other substances which can act as proteinaceous drugs.

In using radioisotopes certain isotopes may be more preferable than others depending on such factors, for example, as tumor distribution and mass as well as isotope stability and emission. Depending on the type of malignancy present come emitters may be preferable to others. In general, alpha and beta particle-emitting radioisotopes are preferred in immunotherapy. For example, if an animal has solid tumor foci a high energy beta, emitter capable of penetrating several millimeters of tissue, such as $^{90}Y$, may be preferable. On the other hand, if the malignancy consists of single target cells, as in the case of leukemia, a short range, high energy alpha emitter such as $^{212}Bi$ may be preferred. Examples of radioisotopes which can be incorporated in the compositions of the invention for therapeutic purposes are $^{125}I$, $^{131}I$, $^{90}Y$, $^{67}Cu$, $^{212}Bi$, $^{211}At$, $^{212}Pb$, $^{47}Sc$, $^{109}Pd$ and $^{188}Re$. Other radioisotopes which can be incorporated into the compositions of the invention are within the skill in the art.

Lectins are proteins, usually isolated from plant material, which bind to specific sugar moieties. Many lectins are also able to agglutinate cells and stimulate lymphocytes. Other therapeutic agents which can be used therapeutically with the biodegradable compositions of the invention are known, or can be easily ascertained, by those of ordinary skill in the art.

The term "therapeutically effective" as it pertains to the compositions of the invention means that the therapeutic agent is present at concentrations sufficient to achieve a particular medical effect for which the therapeutic agent is intended. Examples, without limitation, of desirable medical effects which can be attained are chemotherapy, antibiotic therapy, birth control, and regulation of metabolism.

"Therapeutic-agent bearing" as it applies to the compositions of the invention denotes that the composition incorporates a therapeutic agent which is 1) not bound to the polymeric matrix, or 2) bound within the polymeric backbone matrix, or 3) pendantly bound to the polymeric matrix, or 4) bound within the polymeric backbone matrix and pendantly bound to the polymeric matrix. When the therapeutic agent is not bound to the matrix, then it is merely physically dispersed with the polymer matrix. When the therapeutic agent is bound within the matrix it is part of the poly(phosphoester) backbone (R'). When the therapeutic agent is pendantly attached it is chemically linked through, for example, by ionic or covalent bonding, to the side chain (R) of the matrix polymer. In the first two instances the therapeutic agent is released as the matrix biodegrades. The drug can also be released by diffusion through the polymeric matrix. In the pendant system, the drug is released as the polymer-drug bond is cleaved at the bodily tissue.

A combination of more than one therapeutic agent can be incorporated into the compositions of the invention. Such multiple incorporation can be done, for example, 1) by substituting a first therapeutic agent into the backbone matrix (R') and a second therapeutic agent by pendant attachment (R), 2) by providing mixtures of different poly (phosphoesters) which have different agents substituted in the backbone matrix (R') or at their pendant positions (R), 3) by of unbound therapeutic agents with the poly (phosphoesters) which is then formed into the composition, 4) by use of a copolymer with the general structure wherein m or n can be from about 1 to about 99% of the polymer, or 5) by combinations of the above.

The concentration of therapeutic agent in the composition will vary with the nature of the agent and its physiological role and desired therapeutic effect. Thus, for example, the concentration of a hormone used in providing birth control as a therapeutic effect will likely be different from the concentration of an anti-tumor drug in which the therapeutic effect is to ameliorate a cell-proliferative disease. In any event, the desired concentration in a particular instance for a particular therapeutic agent is readily ascertainable by one of skill in the art.

The therapeutic agent loading level for a composition of the invention can vary, for example, on whether the therapeutic agent is bound to the poly(phosphoester) backbone polymer matrix. For those compositions in which the therapeutic agent is not bound to the backbone matrix, in which the agent is physically disposed with the poly(phosphoester), the concentration of agent will typically not exceed 50 wt. %. For compositions in which the therapeutic agent is bound within the polymeric backbone matrix, or pendantly bound to the polymeric matrix, the drug loading level is up to the stoichiometric ratio of agent per monomeric unit.

The term "transient structural prosthesis" when used to describe the compositions of the invention means a prosthesis which is biodegradable with time and provides a structural function in the individual such as, for example, as a vascular graft, suture and bone plate.

A poly(phosphoester) composition of the invention can function simultaneously both as a transient structural prosthesis and as a therapeutic agent-bearing composition. An example of this would be a suture bearing a therapeutic agent such as, for example, an antibiotic, or, alternatively, a bone plate incorporating a growth factor.

A novel advantage of the polymers of the invention is the availability of functional side groups which allow the chemical linkage of therapeutic agents to the polymers. For example, drugs with carboxyl groups can be coupled to the phosphorous atom via an ester bond, which is hydrolyzable (Eq. 4). The rate of therapeutic agent release will then be dependent on the hydrolytic cleavage of the polymer therapeutic agent conjugate. This pendant delivery system has the advantage of attaining a high drug loading level. Therapeutic agents which exist in the liquid state can also be accommodated.

Alternatively, therapeutic agents containing two hydroxyl groups can be directly incorporated into the backbone of the polymers (Eq. 5). For instance, steroids such as estradiol can be reacted with dichlorophosphates to form the polymer. Other therapeutic agents can also be derivatized for incorporation into the backbone. For instance, a drug with two amino groups can be reacted with the carboxyl group of a hydroxyl carboxylic acid. The hydroxyl groups can then be used to form the poly(phosphate ester). A sustained delivery is then effected by hydrolysis of the polymeric prodrug.

The poly(phosphoesters) of the invention can be synthesized using such polymerization methods as bulk polymerization, interfacial polymerization, solution polymerization, and ring opening polymerization (Odian, G., *Principles of Polymerization*, 2nd ed., John Wiley & Sons, New York, 1981). Using any of these methods, a variety of different synthetic polymers having a broad range of mechanical, chemical, and biodegradable properties are obtained; the differences in properties and characteristics are controlled by varying the parameters of reaction temperatures, reactant concentration, types of solvent, and reaction time.

The poly(phosphoesters) of the invention can range in molecular weight from about 2,000 to about $10^6$ containing from about 10 to about 10,000 monomeric units.

All of the compositions useful as prostheses or implants are synthetic poly(phosphoester) compositions which share such characteristics as predictable and controllable degradation rates, biocompatibility and biodegradability, mechanical strength, and ease of fabrication.

The rate of biodegradation of the poly(phosphoester) compositions of the invention may also be controlled by varying the hydrophobicity of the polymer. The mechanism of predictable degradation preferably relies on either group R' in the poly(phosphoester) backbone being hydrophobic for example, an aromatic structure, or, alternatively, if the group R' is not hydrophobic, for example an aliphatic group, then the group R is preferably aromatic.

The rates of degradation for each poly(phosphoester) composition are generally predictable and constant at a single pH. This permits the compositions to be introduced into the individual at a variety of tissue sites. This is especially valuable in that a wide variety of compositions and devices to meet different, but specific, applications may be composed and configured to meet specific demands, dimensions, and shapes—each of which offers individual, but different, predictable periods for degradation.

When the composition of the invention is used for long term delivery of a therapeutic agent a relatively hydrophobic backbone matrix, for example, containing bisphenol A, is preferred. It is possible to enhance the degradation rate of the poly(phosphoester) or shorten the functional life of the device, by introducing hydrophilic or polar groups, into the backbone matrix. Further, the introduction of methylene groups into the backbone matrix will usually increase the flexibility of the backbone and decrease the crystallinity of the polymer. Conversely, to obtain a more rigid backbone matrix, for example, when used orthopedically, an aromatic structure, such as a diphenyl group, can be incorporated into the matrix. Also, the poly(phosphoesters) can be crosslinked, for example, using 1,3,5-trihydroxybenzene or $(CH_2OH)_4C$, to enhance the modulus of the polymer. Similar considerations hold for the structure of the side chain (R).

The entire class of poly(phosphoesters) are biocompatible and biodegradable. In view of their intended function as a therapeutic agent-bearing implant or prosthesis to be introduced into a subject in vivo, it is desirable that these compositions be essentially non-inflammatory, and non-immunogenic.

The use of the poly(phosphoesters) of the invention as an implant which also functions as a therapeutic agent-bearing polymeric composition, for example, subcutaneously or in various body cavities, is particularly useful in cases where chronic administration of drug over periods ranging from days to years is required. Examples of drugs which can be used in this manner include insulin for diabetes, pilocarpine for glaucoma, immune agents for various diseases and allergies, contraceptive steroids, narcotic antagonists, antibiotics, anticancer, and antihypertensive drugs.

Subcutaneous implantation is currently one of the most popular routes used for sustained drug delivery. This is partly due to the simplicity of the surgical procedures involved in implantation and removal, and the relatively favorable absorption site offered compared to the oral or percutaneous routes. Surgery could be viewed as a disadvantage, however, depending on the patient and the location and frequency of implantation. It can be avoided in some cases by injecting the implant directly into subcutaneous tissue, provided the implant is capable of being delivered through a syringe. This is the method used for many of the sustained-release insulin products.

Implantation using a syringe is particularly effective when the composition of the invention is in the form of microspheres which can be suspended in a pharmaceutical buffer and introduced via the syringe to the desired site.

For example, compositions in the form of microspheres incorporating cortisone could be injected into the region of an inflammatory joint or muscle.

The use of the biodegradable polymers of the invention to act as a matrix for the release of a therapeutic agent from subcutaneously implanted compositions offers several advantages over prior art compositions. The most obvious is that no surgical removal of the device is necessary after it has fulfilled its function. Also, an additional mechanism for release of drug is provided by degradation. Complete delivery and, thus, maximal absorption occurs after the device has degraded.

The mechanism of release of therapeutic agent from biodegradable slabs, cylinders, and spheres has been described by Hopfenberg (in Controlled Release Polymeric Formulations, pp. 26-32, Paul, D. R. and Harris, F. W., Eds., American Chemical Society, Washington, D.C., 1976). A simple expression describing additive release from these devices where release is controlled primarily by matrix degradation is $$M_t/M_\infty = 1 - [1 - k_0 t/C_0 a]^n$$

where $n=3$ for a sphere, $n=2$ for a cylinder, and $n=1$ for a slab. The symbol a represents the radius of a sphere or cylinder or the half-thickness of a slab. $M_t$ and $M_\infty$ are the masses of drug released at time t and at infinity, respectively.

Biodegradable subcutaneous implants can also be used, for example, for the delivery of narcotic antagonists, steroids, and anticancer agents. Narcotic antagonists, such as naltrexone, cyclazocine, and naloxone, are therapeutically useful in the postdetoxification stage of rehabilitation of drug-dependent patients. Steroids which can be used include contraceptives (for example, progesterone), anti-inflammatory agents (for example, dexamethasone), and anabolics (for example, estradiol). Anticancer agents which can be used include cyclophosphamide, doxorubicin, and cisplatin.

Intravaginal implants are used for the sustained release of contraceptive steroid hormones due to the more favorable site of absorption offered by the vaginal mucosa relative to the oral route for these drugs. First-pass hepatic metabolism, which inactivates many steroid hormones, and gastrointestinal incompatibility are avoided by using the vaginal route. In addition, the vaginal route allows self-insertion ensuring better patient compliance. More stable poly(phosphoesters) are preferred in this usage.

The intrauterine device (IUD) is one of the more popular methods of contraception which can utilize the compositions of the invention. Initial investigations involving nonmedicated IUDs revealed that the larger the device, the more effective it was in preventing pregnancy. Unfortunately, large devices caused increased incidences of uterine cramps, bleeding, and expulsion. The effort to improve intrauterine contraception and avoid previously demonstrated side effects has led to the development of medicated IUDs. More stable poly(phosphoester) are preferred in this usage. Two classes of agents have been used in IUDs of this type: contraceptive metals, such as copper, and steroid hormones, such as progesterone.

The compositions of the invention are also useful in the treatment of glaucoma. Chronic open-angle glaucoma usually requires therapy for the lifetime of the patient with a miotic agent such as pilocarpine, for control of intraocular pressure. Conventional pilocarpine therapy requires instillation of eyedrops four times a day. Hence, compositions of the invention incorporating an anti-glaucoma agent such as pilocorpine would require less frequent and more sustained administration.

In addition to the embodiments described above, compositions comprising the poly(phosphoesters) of the invention can be used for agricultural purposes. This can be accomplished by substituting for the therapeutic agent, without limitation, a pesticide, a plant growth horomone, a fungicide, a fertilizer, and the like, others of which are known or readily ascertainable to those of skill in the art.

The above disclosure generally describes the present invention. A further understanding can be obtained by reference to the following specific examples which are provided herein for purposes of illustration only, and are not intended to be limiting unless otherwise specified.

EXAMPLE 1

General Polymer Synthesis Techniques

Four different methods were used for the synthesis of the phosphorus-containing polymers: bulk polycondensation, solution polymerization, interfacial polycondensation, and ring-opening polymerization. In these syntheses, care was taken to eliminate traces of moisture from the system. The reaction vessels were carefully dried and purged with dry nitrogen before use. The nitrogen stream was passed through a Deoxo purifier for oxygen removal. The polymerization, except in the case of interfacial polycondensation, was conducted under nitrogen sweep. All reactants were fractionally distilled under vacuum or recrystallized before use. In particular, the phosphorus diacid chlorides were freshly distilled before each experiment. Solvents were dried over molecular sieves. The phase transfer catalysts of cetyltrimethylammonium chloride and crown ether 18 were used for the interfacial polycondensation. Lewis acids of ferric chloride and magnesium chloride were used for melt-polycondensation. For ring-opening polymerization, t-BuOK or (i-$C_4H_9$)$_3$Al were used as initiators. In reactions involving diols oxidizable to quinones in base the procedures were performed in the dark, and small amounts of sodium hydrosulfite were added to the interfacial polycondensation to prevent oxidation of the diol.

A. Melt-Polycondensation

In melt, or bulk, polycondensation the phosphonic or phosphoric dichloride is mixed with the diol in the absence of solvent. A Lewis acid catalyst ($FeCl_3$, $MgCl_2$, etc.) is added and the mixture is heated, often under vacuum or nitrogen blanket, to remove the Hcl formed. These somewhat vigorous conditions can lead to chain acidolysis (or hydrolysis if water is present). Unwanted, thermally-induced side reactions such as adventitious crosslinking can also occur if the polymer backbone is susceptible to hydrogen atom abstraction or oxidation with subsequent macroradical recombination. On the positive side, this technique avoids solvents and large amounts of other additives, thus making purification more straight-forward. It can also provide polymers of reasonable molecular weight.

B. Solution-Polycondensation

Solution polycondensation requires that both the diol and the phosphorus component be soluble in a common solvent. Typically, a chlorinated organic solvent was used and the reaction run in the presence of a stoichiometric amount of an acid acceptor. The product was then isolated from the solution by precipitation and purified to remove the hydrochloride salt. Although longer reaction times may be necessary, generally much milder conditions are used relative to bulk-reactions. More sensitive functionality can thus be incorporated using this technique.

C. Interfacial-Polycondensation

Interfacial polycondensation potentially yields high molecular weights for these polymers at high reaction rates. Since the interfacial technique is a non-equilibrium method, the critical dependence of high molecular weight on exact stoichiometric equivalence between diol and dichloridate inherent in bulk and solution methods is removed. The limitation of this method is the hydrolysis of the acid chloride in the alkaline aqueous phase. Phosphoro-dichloridates which have some solubility in water are generally subject to hydrolysis rather than polymerization.

D. Ring Opening

Ring-opening polymerization of phosphorus-containing monomers was performed using the technique disclosed in Lapienis, et al., *Journal of Polymer Science, Part A: Polymer Chemistry*, 25:1729, 1987 and Pretula, et al., *Macromolecules*, 19:1797, 1986. This technique is particularly useful in producing high molecular weight polymers.

EXAMPLE 2

Preparation of Poly(Phosphoesters)

A. Using the melt-condensation technique, a poly(phosphate ester) having the structure disclosed in Equation 6 was produced. Ethyl phosphorodichloridate was slowly added to a magnetically stirred mixture of an equimolar amount of ethylene glycol containing 2 mole percent of $FeCl_3$ cooled to $-20°$ C. The flask was connected to a vacuum pump through a trap to remove HCl. When the addition was complete, the temperature was gradually raised to 120° C. over a seven hour period. The mass was then cooled to room temperature, dissolved in methanol, and precipitated into ether.

(Eq. 6)

B. Using the solution-polycondensation technique, a poly(phosphoester) with the structure disclosed in Equation 7 was produced.

A solution of recrystallized bisphenol-A (10.0 g, 43.8 mmol) and dried pyridine (7.62 g, 2.2 equiv.) in 100 ml of dried methylene chloride was cooled to 5° C. in a 500 ml three-necked flask equipped with a paddle stirrer, thermometer, and gas inlet and exit tubes. Under positive pressure of dry nitrogen, a solution of 7.14 g (43.8 mmol) of freshly distilled ethyl phosphorodichloridate in 25 ml of methylene chloride was added from an addition funnel over a period of 30 minutes. An increase in viscosity was noted during the addition. When the addition was complete, the temperature was allowed to rise to 25° C. and stirring was continued under nitrogen for 18 hours. The precipitate of pyridine hydrochloride was removed by filtration and the filtrate was washed twice with 40 ml of distilled water. After drying over $CaCl_2$, the methylene chloride solution was concentrated and precipitated into 500 ml of petroleum ether. The oil isolated was dried on a vacuum line at room temperature for 16 hours to give 8.42 g (60.4% yield) of the poly(phosphate) as a crisp white foam having $M_W = 17,000$ (by GPC relative to polystyrene in chloroform).

(Eq. 7)

C. The poly(phosphoester) of Equation 8 was produced using the interfacial polycondensation technique.

A solution of recrystallized bisphenol-A (10.0 g, 43.8 mmol) and sodium hydroxide (3.66 g, 1.04 equiv.) in 65 ml of distilled water was prepared; 1.12 g (2 mole percent) of a 25% aqueous solution of cetyltrimethylammonium chloride (CTMAC) was then added with stirring. Separately a solution of phenylphosphonodichloridate (8.59 g, 43.8 mmol) in 60 ml. of dried methylene chloride was prepared in a dropping funnel and kept under nitrogen. Both of these solutions were then cooled to 0° C. The aqueous solution was transferred to the jar of a 1 L Waring commercial blender; low speed mixing was begun immediately. The organic solution was run into the agitated solution from the funnel through a hole in the cap over a one-minute period. The mixture was blended for four minutes, producing a thick, milky emulsion with a temperature of 35° C. After separating the layers in a separatory funnel, the lower organic layer was washed with 30 ml of water, dried over $CaCl_2$, and precipitated into 750 ml of petroleum ether to give a fibrous, powdery solid. The solid was isolated by filtration, reprecipitated in the same manner, isolated again, and dried on a vacuum line at room temperature for 16 hr. to give the polyphosphonate (15.1 g, 98.4%) as a fine powder.

(Eq. 8)

-continued

Additional examples of some of the poly(phosphoesters) which have been synthesized using the above techniques and their properties are shown in Table 1.

TABLE 1

| Polymer | R | R' | Method | Properties |
|---|---|---|---|---|
| I | —OC$_2$H$_5$ | 1 | A | dark brown solid, swells in hot water |
|  | —OC$_2$H$_5$ | 1 | C | white powder; M$_n$ = 3879, M$_w$ = 35365, T$_s$ = 60-70° C. |
|  | —OC$_2$H$_5$ | 1 | B | M$_n$ = 3920 |
| II | —OC$_2$H$_5$ | 2 | C | T$_m$ = 110-130° C.; solution in chloroform |
| III | —OC$_2$H$_5$ | 3 | C | [ ] = 0.16 dL/g, soluble in DMF |
| IV | —OC$_2$H$_5$ | 4a | A | waxy solid, T$_m$ = 30-35° C., soluble in pH 7.4 phosphate buffer, slow decomposition in air (spongy) |
| V | —OC$_2$H$_5$ | 4b | A | solid swells up to 560% in 48 hours in pH 7.4 phosphate buffer, swells in MeOH and chloroform, T$_m$ = 140-220° C. |
| VI | —OC$_2$H$_5$ | 4c | A | swells in buffer, T$_m$ = 90° C. |
| VII | —OC$_2$H$_5$ | 4d | A | water soluble, T$_m$ = 55-65° C. |
| VIII | —C$_6$H$_5$ | 1 | C | M$_n$ = 4917, M$_w$ = 33867 |
| IX | —OC$_6$H$_5$ | 1 | C | M$_n$ = 3745, M$_w$ = 34860 |
| X | —OC$_6$H$_5$(NO$_2$) | 1 | C | yellow sticky material |

A = melt-condensation with MgCl$_2$ as catalyst
B = solution polymerization in refluxing methylene chloride
C = aqueous interfacial condensation (CH$_2$Cl$_2$—H$_2$O) with phase transfer catalysts for 4a, m = 14.
for 4b, m = 34
for 4c, m = 77
for 4d, m = 182

D. The ring-opening technique was used to produce the poly(phosphoester) shown in Equation 9. Using dioxa-phosphorinane at a concentration of 7.0 mol/L in methylene chloride, a polymer with a number average molecular weight of over 100,000 was obtained as a white, powdery material in about 50% yield when triisobutylaluminum (0.03M) was used as the initiator at 25° C. after a 24 hour reaction (Eq. 9). The difficulty of this technique is the preparation of the pure cyclic monomers. In order to maintain a favorable thermodynamic driving force for the ring-opening reaction, the monomer is confined to aliphatic and non-bulky groups. The cyclic monomer also should not contain acidic protons.

(Eq. 9)

EXAMPLE 3

Comparative Release Rates of Compounds from Pendant and Matrix Systems

Poly(phosphoester) compositions were prepared which contained benzoic acid, aniline, thiophenol, or p-nitrophenol in pendant position in combination with an aliphatic backbone, as shown in Equation 10 below.

R=benzoic acid, aniline, thiophenol, or p-nitrophenol

The ring-opening polymerization technique was used to prepare poly(2-chloro-2-oxo-1,3,2-dioxaphosphite). To prepare the cyclic monomer 2-hydro 2-oxo-1,3,2-dioxaphosphite, a solution (100 ml) of 1,3-propanediol (0.165 mole) and triethylamine (TEA) (0.33 mole) in benzene was added dropwise to vigorously stirred anhydrous benzene (200 ml) at 0° C. under nitrogen atmosphere. Phosphorus trichloride (0.165 mole) in anhydrous benzene (200 ml) was then added. After a reaction of two hours and the TEA HCl salt filtered off, a mixture of water (0.2 mole), TEA (0.2 mole), and tetrahydrofuran(10 ml) were added dropwise. After two hours of vigorous agitation, the solvent was removed under reduced pressure. The residue was separated by flash chromatography using silica as the packing material and chloroform/toluene (50:50) as the mobile phase. The purity of the monomer was checked by thin layer chromatography (TLC). The TLC plates were developed by iodine vapor for visualization.

The polymers were synthesized by anionic polymerization of 2-hydro-2-oxo-1,3,2-oxaphosphorinane. The anionic polymerization was conducted in methylene chloride at −15° C. for 48 hours under nitrogen atmosphere. A 1 mole % of i-Bu$_3$Al was used as the anionic initiator. The polymer was isolated by repeated precipitation into dried benzene. Chlorination of the polymer was achieved by passing dried chlorine through a solution of the polymer in methylene chloride until a persistent yellow color was obtained (about three hours). The excess chlorine was then removed by vacuum at room temperature. The polymers was characterized by GPC, intrinsic viscosity, FT-IR, and FT-NMR.

Figure 1A:
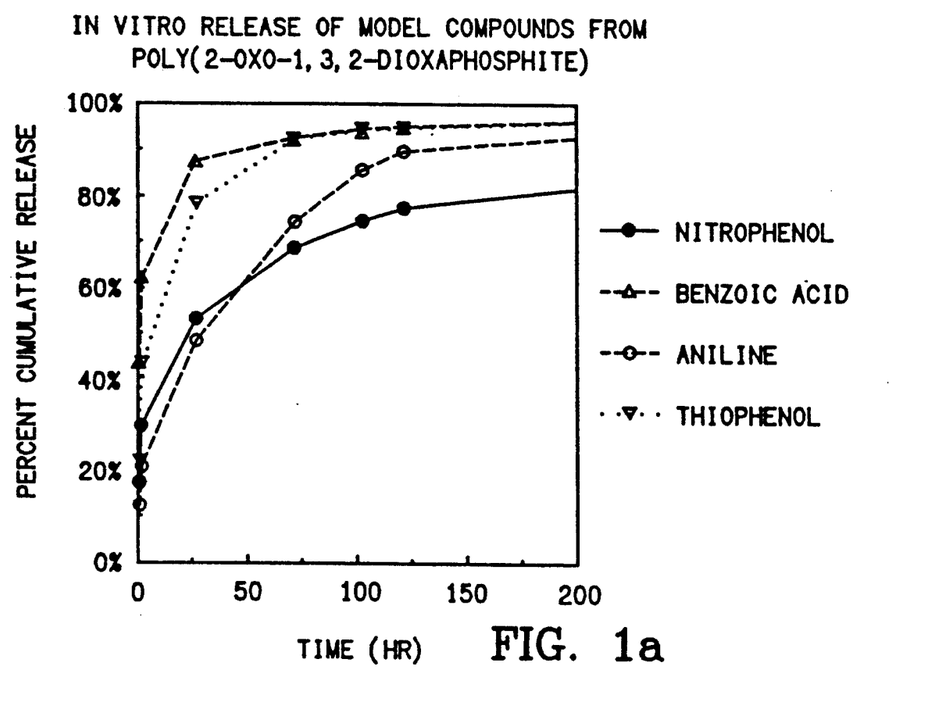
FIG. 1(a) shows the in vitro release of different pendant R groups when attached to a poly(2-oxo-1,3,2-dioxaphosphite) backbone matrix.

After chlorination, the compounds were linked to the side chain of the polymer via dehydrochlorination. The chemical structures containing different R groups were all confirmed by FTIR and UV spectrophotometry. FIG. 1a shows the vitro release of the R groups from polymer.

The drug release rate was dependent on the stability of the linkage bond. For instance, benzoic acid was bound to the polymer via a phosphoric anhydride bond, which is extremely water labile. Consequently, a high release rate was seen. The model drugs are all water soluble compounds, which in a diffusion-controlled release system would be depleted very quickly.

Figure 1B:
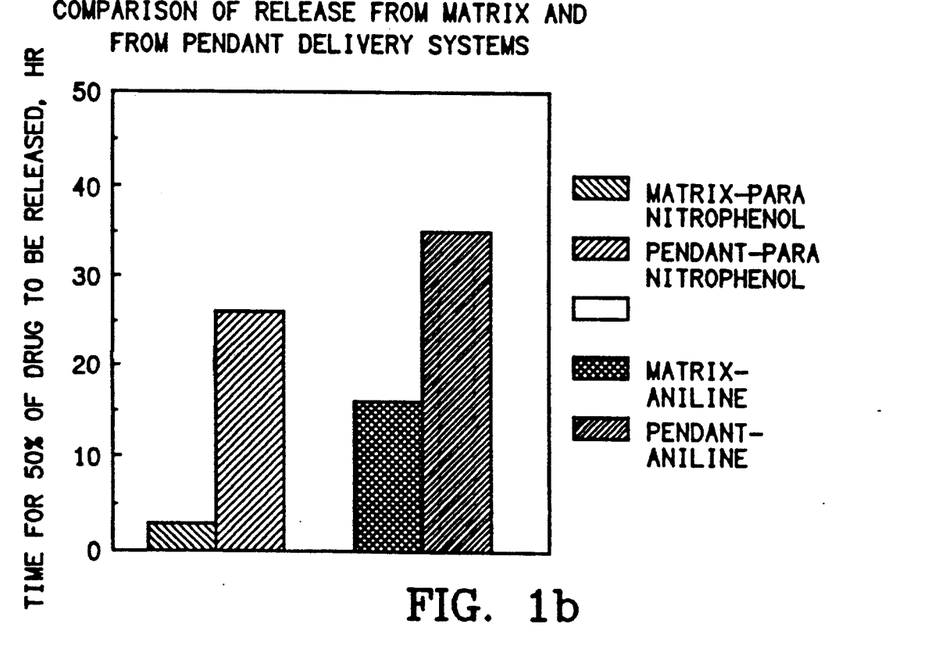
FIG. 1(b) compares the release of nitrophenol and aniline from a composition matrix system and a pendant system.

Shown in FIG. 1b is the comparison of the release of p-nitrophenol and aniline from a matrix system (in which the drug is just physically dispersed in the polymer and compression molded into a disc) and that released from the pendant system (in which the polymer-drug conjugates are compression molded to the same dimension). The time it took for 50% of the drug to be released from the polymer-drug conjugate was significantly longer, showing that the pendant system is indeed capable of prolonging the release of hydrophilic drugs through a phosphate ester or a phosphoroamide bond.

EXAMPLE 4

Comparison of Degradation Rates of Various BPA Polymers

Various poly(phosphoesters) were prepared having a bisphenol A (BPA) backbone and their rates of in vitro degradation compared.

These polymers were prepared in a manner similar to that disclosed in Example 1 B or C except for the substitutions to the phosphochloridate. The four side chains of Table 2 were commercially available from Aldrich Chemicals.

In order to use side chains of other structures it is possible to start with the phosphorochloride of where R is the desired structure. The monomer can be obtained either commercially or custom synthesized. Such synthesis can be carried out, for example, by reacting phosphorous oxychloride with the desired structure in the presence of a acid acceptor in an organic solvent, according to the general equation:

The polymers prepared had the structures indicated in Table 2.

TABLE 2

Backbone:

| R | Designation |
|---|---|
| —OC$_2$H$_5$ | BPA—EOP |
| —C$_2$H$_5$ | BPA—EP |
| —O-phenyl | BPA—POP |
| —phenyl | BPA—PP |

These polymers were then placed in pH 12 phosphate buffer and their relative rates of degradation determined.

The degradation experiments were conducted in 0.1M phosphate buffer (pH 12). The polymers were compression molded into discs (1 cm ×2 mm), placed in 50 ml of pH 12 buffer, and incubated at 37° C. The release kinetics were followed by measuring the concentrations of the buffer solution by HPLC. The weight loss of the discs as a function of time was also recorded.

Figure 2:
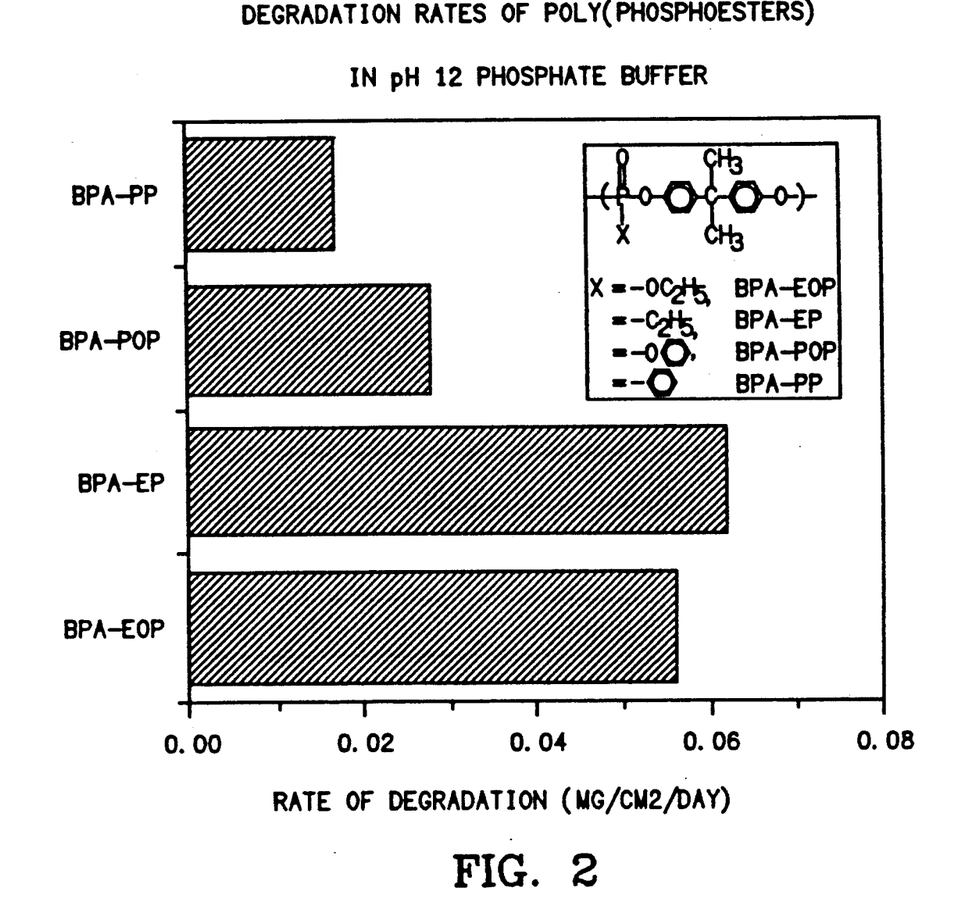
FIG. 2 compares the degradation rates of various a poly(phosphoesters).

The results are illustrated in FIG. 2. As expected, the hydrolysis was base catalyzed. In pH 7.4 buffer at 37° C.,$_9$ BPA-EOP lost less than 5% of its weight in 10 days. In a 0.1M NaOH solution at 37° C.,$_9$ the polymer completely decomposed in less than one week.

EXAMPLE 5

Comparison of Non-Pendant Drug Release Rates from BPA Polymers

Poly(phosphoesters) with a bisphenol A backbone and different side chains were prepared as described in Example 4 and compared in terms of their in vitro release of different drugs.

In a first experiment compositions of BPA-PP, BPA-POP, BPA-EP, and BPA-EOP incorporating cortisone or lidocaine were compared.

Drugs were incorporated into the matrix by compression molding. The polymer was ground and sieved into a particle size range below 90 microns. Drugs were sieved to the same particle size range and blended in a Vortex mixer with the polymer powder. The mixture was pressed into a disc (10 mm×2 mm) through a mold, at a pressure of 150 Kpsi and room temperature for 10 min. Such a high molding pressure is useful in forming a compact matrix for desirable sustained release. The molds were specifically made with carbon and heat treated plungers to withstand the high pressure. The poly(phosphoester)-drug conjugates are similarly molded for implantation.

A solvent evaporation technique was used to prepare the microspheres. A solution of 2 g of polymer and 0.4 g of drug in 20 ml of methylene chloride was prepared. The mixture was emulsified in 150 ml of water containing 0.5 wt. % of poly(vinyl alcohol) in a homogenizer. The methylene chloride in the emulsion was evaporated over a period of one hour at room temperature at a reduced pressure of 40 mm Hg. The microspheres thus obtained were quickly washed with cold water and filtered. After drying, the microspheres were sieved to a narrow size fraction before use. This technique can be used to encapsulate, for example, such organic substances as sucrose and nerve growth factor.

Release experiments were conducted in a 0.1M pH 7.4 phosphate buffer containing 0.02 wt. % of gentamicin sulfate to inhibit bacterial growth. The drug-loaded matrices were placed in 10 ml of buffer in 20 ml vials and incubated at 37° C. The release kinetics were followed by measuring the concentrations of the buffer solutions by scintillation counting and high pressure liquid chromatography (HPLC). HPLC analysis was used to determine the degradation rate of the matrix and to check the chemical purity of the drug. To approximate perfect sink conditions, the frequency of replacement of the buffer solutions was adjusted during the course of the release study to ensure that the drug concentration in buffer was below 20% of its saturation value. In situations where the release rates are rapid (100 percent release in less than 2 days) and when dealing with microspheres, the experiment was conducted in a flow system. The matrices or the microspheres were placed in a glass vial equipped with a glass filter and Teflon stopcock in the bottom. A counter-gravitational flow of 0.1M pH 7.4 phosphate buffer was passed through the sample at a rate of 0.5 ml./min. Both the buffer reservoir and the release vessel were immersed in a 37° C. bath. The eluent was collected every hour and subjected to chromatographic and spectro-photometric analyses.

Figure 3:
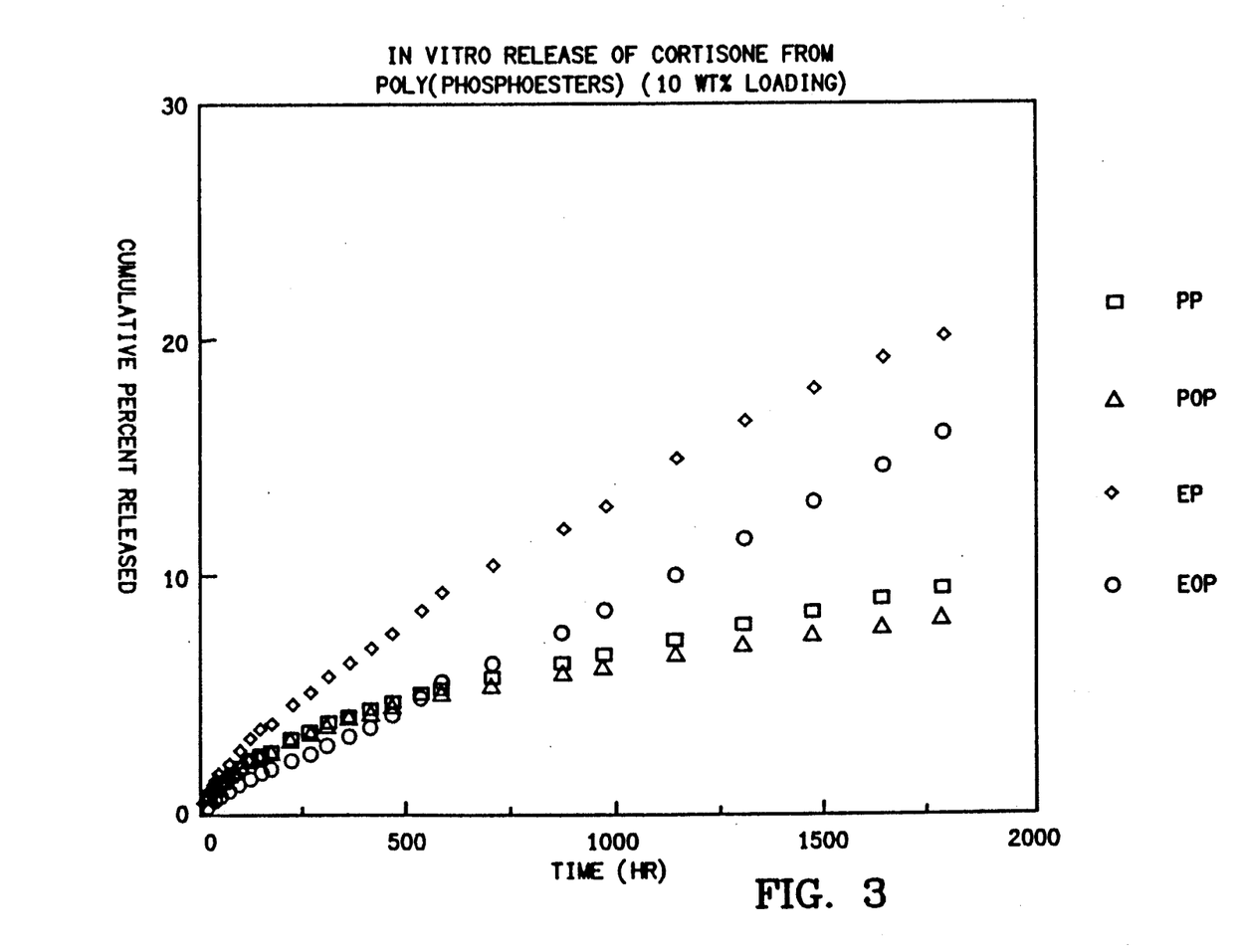
FIG. 3 shows the release rates of non-pendant cortisone from various poly(phosphoester) matrices.
Figure 4:
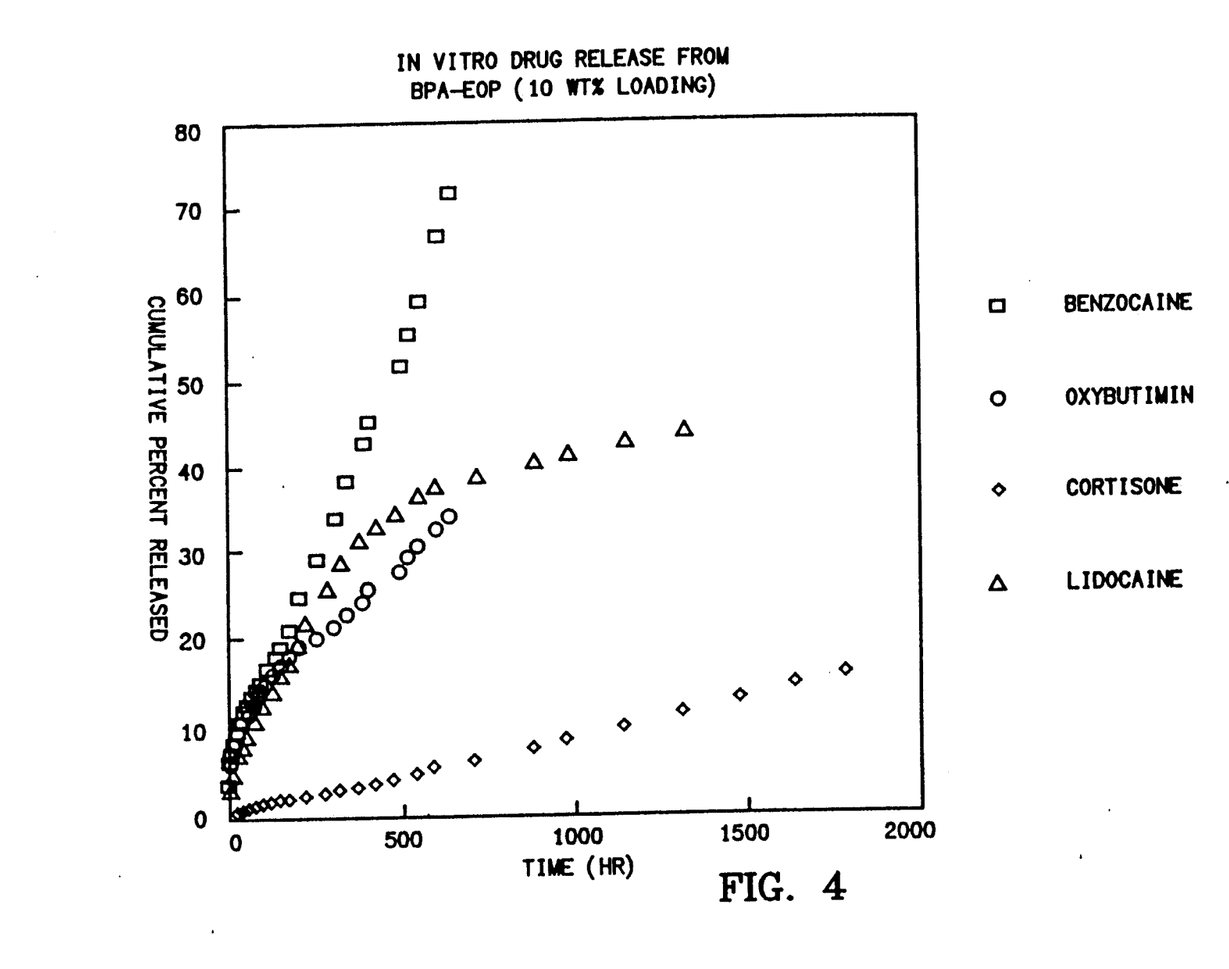
FIG. 4 illustrates the release rates of four different drugs form the same BPA polymer matrix.

The release kinetics are shown for cortisone in FIG. 3. The data indicate that the release rate was dependent on the chemical structure of the side chain (R). This is the first study which demonstrates systematically that the variation of the side chain of a biodegradable polymer can control the release rates. The EOP and EP side chains generally give faster release rates because they are less hydrophobic than the POP and PP structures. Noteworthy is the constant release of cortisone from the polymers.

In a second experiment, the release kinetics of various non-pendant drugs were measured for BPA-EOP derived matrix compositions. As shown in FIG. 5, all four drugs were release in intact form from the polymer as determined by HPLC. These release profiles show that, in general, drugs of higher water solubility have higher release rates.

EXAMPLE 6

Preparation of Pendant 5-Fluorouracil Compositions

A mixture of 5-FU (7 mmole) and 1,1,1,3,3,3-hexamethyldisilazane (30 ml) were heated at reflux temperature for 20 hours in the presence of a catalytic amount of ammonium sulphate to derivatize 5-FU. Evaporation of the mixture under reduced pressure resulted in the formation of 2,4-bis-o-trimethylsilyl-5-fluorouracil. To obtain the final polymer-drug conjugate, the chlorinated poly(phosphoester) (5g) in methylene chloride (20 ml) was reacted with the 5-FU derivative in the presence of a stoichiometric amount of pyridine. After stirring for 18 hours at room temperature, 15 ml of methanol was added. After evaporation of the solvent, the residue was redissolved in dimethyl formamide and repeatedly precipitated into acetone. Linking of iodoaminopurine (IAP) to the polymer can be achieved in a similar manner by taking advantage of the facile reaction between the primary amine of the drug and the chlorine in the side chain of the polymer.

In the in vitro release studies (as in Example 5), a sustained release of 5-FU was observed for at least 7 days and chemical integrity of the 5-FU was confirmed by HPLC. This release rate is far superior to similar studies with 5-FU pendently attached to a polyhydride carrier where nearly complete release occurred after only 2 days.

The invention now being fully described, it will be apparent to one of ordinary skill in the art that many changes and modifications can be made without departing from the spirit or scope of the invention.

I claim:

1. A pharmaceutical composition comprising an effective amount of a therapeutic agent, together with a delivery vehicle, wherein the vehicle comprises a polymer represented by the formula:

wherein n ranges from about 10 to $10^5$, R is a therapeutic agent capable of being released in a physiological environment, and R' is selected from the group consisting of:

wherein $R_1$ is alkyl, halogen, nitro, hydroxyl, amino, carboxyl, alkoxy, or combinations thereof, $R_2$ is oxygen or N—$CH_3$, and a ranges from 2 to 6, b ranges from 10 to 100, d ranges from 2 to 16, f ranges from 1 to 6, and m ranges from 1 to 2.

2. The pharmaceutical composition according to claim 1, wherein the composition is suitable for providing transient structural prosthesis.

3. A pharmaceutical composition comprising an effective amount of a therapeutic agent, together with a delivery vehicle, wherein the vehicle comprises a polymer represented by the formula:

wherein n ranges from about 10 to about $10^5$, R' is a therapeutic agent capable of being released in a physiological environment, and R is selected from the group consisting of:

$$-NH-R_1, -S-R_1, -O-\overset{O}{\underset{\|}{C}}-R_1$$

$$-OC_pH_{2p+1} \quad -C_pH_{2p+1} \quad -O-CH_2-\underset{CO_2H}{\overset{|}{CH}}-NH_2$$

$$-H, -Cl, -O-R_3$$

wherein $R_1$ is alkyl, halogen, nitro, hydroxyl, amino, carboxyl, alkoxy, or combinations thereof, $R_3$ is or and p ranges from 1 to 16.

4. The pharmaceutical composition according to claim 3, wherein the composition is suitable for providing transient structural prosthesis.

5. A pharmaceutical composition comprising an effective amount of a therapeutic agent, together with a delivery vehicle, wherein the vehicle comprises a polymer represented by the formula:

wherein n ranges from 10 to $10^5$, and both R and R' are therapeutic agents capable of being released in a physiological environment.

6. A pharmaceutical composition comprising an effective amount of a therapeutic agent, together with a delivery vehicle, wherein the vehicle comprises a polymer represented by the formula:

wherein n ranges from about 10 to about $10^5$, R' is selected from the group consisting of:

-continued

R is selected from the group consisting of:

—H, —Cl, —O—R$_3$ wherein R$_1$ is alkyl, halogen, nitro, hydroxyl, amino, carboxyl, alkoxy, or combinations thereof, R$_2$ is oxygen or N—CH$_3$, R$_3$ is  or  and a ranges from 2 to 6, b ranges from 10 to 100, d ranges from 2 to 16, f ranges from 1 to 6, m ranges from 1 to 2, and p ranges from 1 to 16.

7. The pharmaceutical composition according to claim 6, wherein the composition is suitable for providing transient structural prosthesis.

* * * * *